US011166672B2

(12) United States Patent
Whitman

(10) Patent No.: US 11,166,672 B2
(45) Date of Patent: *Nov. 9, 2021

(54) NERVE PROTECTING DISSECTION DEVICE

(71) Applicant: Atlantic Health System, Inc., Morristown, NJ (US)

(72) Inventor: Eric D. Whitman, Mountain Lakes, NJ (US)

(73) Assignee: Atlantic Health System, Inc., Morristown, NJ (US)

( * ) Notice: Subject to any disclaimer, the term of this patent is extended or adjusted under 35 U.S.C. 154(b) by 819 days.

This patent is subject to a terminal disclaimer.

(21) Appl. No.: 16/008,098

(22) Filed: Jun. 14, 2018

(65) Prior Publication Data

US 2019/0076088 A1 Mar. 14, 2019

Related U.S. Application Data

(63) Continuation-in-part of application No. 14/057,358, filed on Oct. 18, 2013, now Pat. No. 10,022,090.

(51) Int. Cl.
*A61B 5/00* (2006.01)
*A61B 17/32* (2006.01)
(Continued)

(52) U.S. Cl.
CPC ............. *A61B 5/4893* (2013.01); *A61B 5/24* (2021.01); *A61B 5/389* (2021.01); *A61B 5/4041* (2013.01);
(Continued)

(58) Field of Classification Search
CPC ......... A61B 5/24; A61B 5/4893; A61B 5/389; A61B 5/4041; A61B 5/6877;
(Continued)

(56) References Cited

U.S. PATENT DOCUMENTS 5,284,153 A 2/1994 Raymond et al.
5,560,360 A 10/1996 Filler et al.
(Continued)

FOREIGN PATENT DOCUMENTS

WO WO 96/39932 12/1996
WO WO 2006/042075 A2 4/2006
(Continued)

*Primary Examiner* — Eun Hwa Kim
(74) *Attorney, Agent, or Firm* — The McHattie Law Firm; Jonathan A. Tyler

(57) ABSTRACT

A nerve mapping system includes an energy based dissection device, a plurality of beacons, and a processing device. The plurality of beacons are disposed in a tissue of a patient. Each beacon is adapted to transmit one or more first electrical signals within the body and receive one or more second energy signals. The processing device is adapted to determine first locations associated with the plurality of beacons, a second location associated with the energy based dissection device, and a third location associated with a nerve within the tissue, based on the one or more second signals, generate a mapping of the first locations, second location, and third location, and cause the first locations, second location, and third location to be displayed on a display device.

18 Claims, 11 Drawing Sheets

(51) Int. Cl.
*A61B 18/14* (2006.01)
*A61B 34/20* (2016.01)
*A61B 5/24* (2021.01)
*A61B 5/389* (2021.01)
*A61B 18/00* (2006.01)
*A61B 18/12* (2006.01)
*A61B 18/04* (2006.01)

(52) U.S. Cl.
CPC .... *A61B 5/4836* (2013.01); *A61B 17/320068* (2013.01); *A61B 18/1402* (2013.01); *A61B 34/20* (2016.02); *A61B 5/6877* (2013.01); *A61B 18/042* (2013.01); *A61B 2018/0044* (2013.01); *A61B 2018/00446* (2013.01); *A61B 2018/00595* (2013.01); *A61B 2018/00601* (2013.01); *A61B 2018/126* (2013.01); *A61B 2018/1253* (2013.01); *A61B 2034/2051* (2016.02); *A61B 2505/05* (2013.01)

(58) Field of Classification Search
CPC .. A61B 2018/0044; A61B 2018/00446; A61B 34/20
See application file for complete search history.

(56) References Cited

U.S. PATENT DOCUMENTS

| | | | |
|---|---|---|---|
| 5,560,372 A | 10/1996 | Cory | |
| 5,775,331 A | 7/1998 | Raymond et al. | |
| 5,928,158 A | 7/1999 | Aristedes | |
| 6,259,945 B1 | 7/2001 | Epstein et al. | |
| 6,478,793 B1* | 11/2002 | Cosman | A61B 18/1477 128/898 |
| 6,500,128 B2 | 12/2002 | Marino | |
| 6,535,759 B1 | 3/2003 | Epstein et al. | |
| 6,564,079 B1 | 5/2003 | Cory et al. | |
| 7,006,863 B2 | 2/2006 | Maddess et al. | |
| 7,214,197 B2 | 5/2007 | Prass | |
| 7,618,380 B2 | 11/2009 | Mallinger et al. | |
| 7,634,315 B2 | 12/2009 | Cholette | |
| 7,717,932 B2 | 5/2010 | McFarlin et al. | |
| 7,865,236 B2 | 1/2011 | Cory et al. | |
| 7,972,284 B2 | 7/2011 | Mallinger et al. | |
| 7,991,463 B2 | 8/2011 | Kelleher et al. | |
| 8,050,769 B2 | 11/2011 | Gharib et al. | |
| 8,068,912 B2 | 11/2011 | Kaula et al. | |
| 8,241,313 B2 | 8/2012 | McFarlin et al. | |
| 8,634,904 B2 | 1/2014 | Kaula et al. | |
| 2002/0077627 A1 | 6/2002 | Johnson | |
| 2003/0195405 A1 | 10/2003 | Marino et al. | |
| 2004/0015205 A1 | 1/2004 | Whitehurst | |
| 2004/0267243 A1 | 12/2004 | Klotz et al. | |
| 2005/0004559 A1 | 1/2005 | Quick | |
| 2006/0085049 A1 | 4/2006 | Cory et al. | |
| 2007/0100334 A1 | 5/2007 | McFarlin et al. | |
| 2008/0077198 A1 | 3/2008 | Webb et al. | |
| 2008/0103416 A1 | 5/2008 | Mallinger et al. | |
| 2009/0054804 A1 | 2/2009 | Gharib et al. | |
| 2009/0054908 A1 | 2/2009 | Zand et al. | |
| 2009/0105604 A1 | 4/2009 | Bertagnoli et al. | |
| 2009/0105788 A1 | 4/2009 | Bartol et al. | |
| 2010/0063376 A1 | 3/2010 | Kartush | |
| 2010/0145178 A1 | 6/2010 | Kartush | |
| 2010/0145222 A1 | 6/2010 | Brunnett et al. | |
| 2010/0179410 A1 | 7/2010 | Prass | |
| 2010/0198099 A1 | 8/2010 | Murphy et al. | |
| 2011/0060243 A1 | 3/2011 | Hausman et al. | |
| 2011/0237974 A1 | 9/2011 | Bartol et al. | |
| 2011/0270120 A1* | 11/2011 | McFarlin | A61B 5/389 600/554 |
| 2012/0123292 A1 | 5/2012 | Fagin | |
| 2016/0206363 A1* | 7/2016 | Mehta | A61M 19/00 |

FOREIGN PATENT DOCUMENTS

| | | |
|---|---|---|
| WO | WO 2006/113394 A2 | 10/2006 |
| WO | WO 2008/124079 A1 | 10/2008 |
| WO | WO 2011/159886 A1 | 12/2011 |
| WO | WO 20-12/106593 A2 | 8/2012 |

* cited by examiner

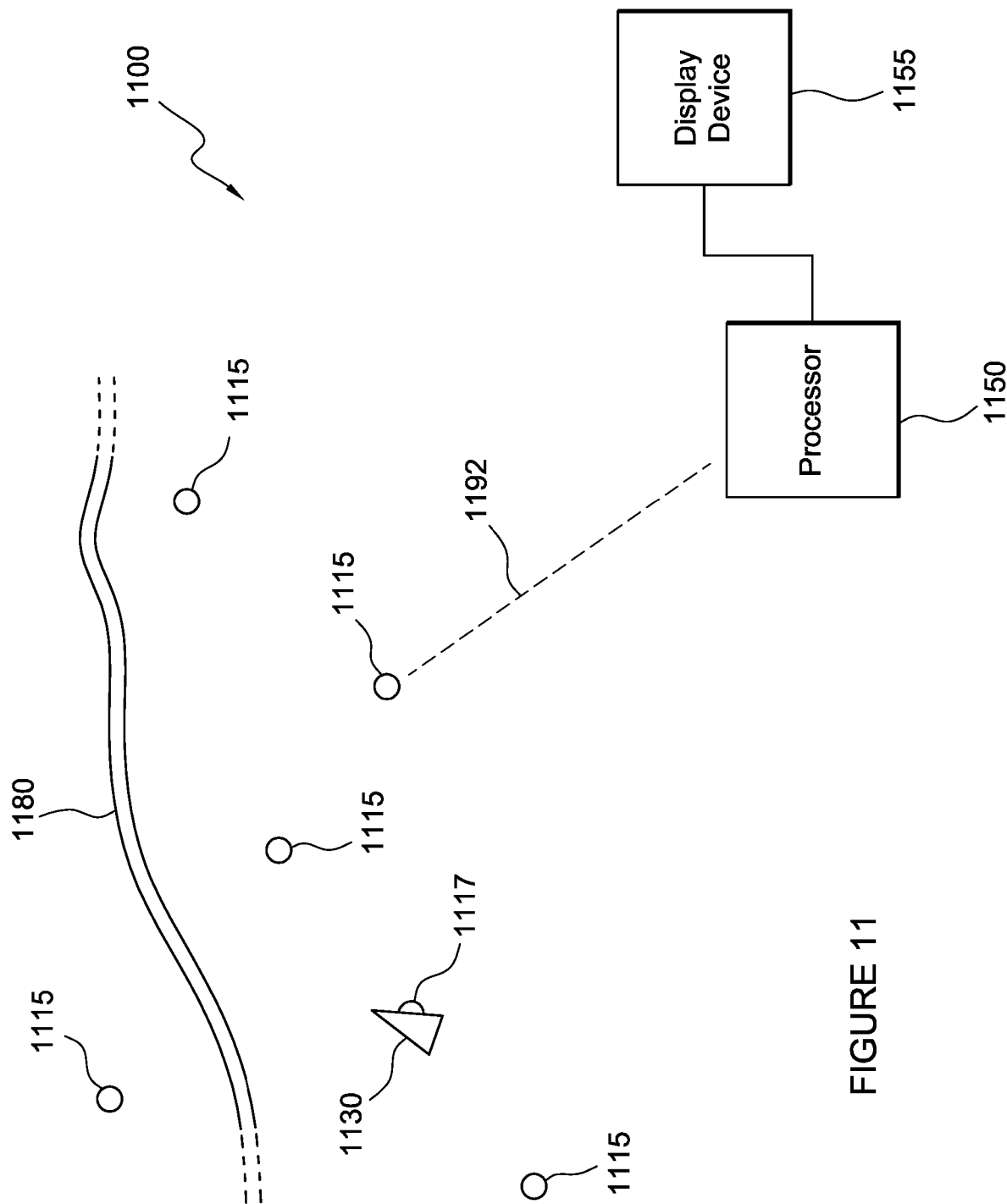

NERVE PROTECTING DISSECTION DEVICE

This application is a continuation-in-part of U.S. patent application Ser. No. 14/057,358, filed Oct. 18, 2013, which is incorporated by reference herein in its entirety and for all purposes.

FIELD OF THE INVENTION

The present invention provides an energy based dissection device that automatically provides a nerve protection function. Specifically, the present invention operatively connects nerve monitoring technology and energy based dissection technology to provide a device that provides energy based dissection functionality that cannot operate, or operates differently, upon receipt of real time information from the nerve monitoring functionality that nerve damage may be imminent in the absence of such safety shutdown. The present invention also creates a real-time graphical display of the nerve, including size and location relative to the energy based dissection device to enable the operator to safely and accurately avoid damaging the nerve. Accordingly, the present invention provides a surgical device that removes human error and reaction time issues which prevent unintended dissection and concomitant nerve damage.

BACKGROUND

Energy based dissection devices are known. For example, U.S. Pat. No. 8,241,313 discloses a surgical cutting instrument for use with a drive motor, and related system and method, is described. The surgical cutting instrument includes an elongated drive member, a cutting tip secured to the drive member, a non-conductive coupling body adapted for connection to a motor assembly, a housing maintaining the coupling body, a fluid coupling assembly and an electrical connector for connection to a stimulating energy source. The electrical connector is in electrical communication with the cutting tip via an electrical pathway.

In another example, Ethicon Endo-Surgery, Inc. discloses their HARMONIC ACE® shears, a sterile, single-patient-use device consisting of an ergonomic grip housing assembly and two hand-controlled power settings. The HARMONIC ACE® shears employ an adaptive tissue technology enabling the generator to actively monitor the instrument during use, allowing the system to respond intelligently to varying tissue conditions. Electrical energy is converted to mechanical energy.

Nerve monitoring devices are also known. For example, U.S. Pat. No. 7,991,463 discloses systems for determining structural integrity of a bone within the spine of a patient, the bone having a first aspect and a second aspect, wherein the second aspect separated from the first aspect by a width and located adjacent to a spinal nerve. A stimulator is configured to generate an electrical stimulus to be applied to the first aspect of the bone. A monitor is configured to electrically monitor a muscle myotome associated with the spinal nerve to detect if an onset neuro-muscular response occurs in response to the application of the electrical stimulus to the first aspect of the bone. An adjuster is configured to automatically increase the magnitude of the electrical stimulus to until the onset neuro-muscular response is detected. Lastly, a communicator is configured to communicate to a user via at least one of visual and audible means information representing the magnitude of the electrical stimulus which caused the onset neuro-muscular response.

In another example, U.S. Pat. No. 7,972,284 discloses a method of preventing nerve damage positional injury during surgery includes providing a nerve damage positional injury pressure monitoring system including a site sensor with a transducer in the form of a transducer element and a ring extending outward from the transducer element, and a monitor connected to the site sensor; adhering the ring of the site sensor to the patient so that the transducer element forms a protective barrier in front of the area of the patient prone to nerve damage positional injury during surgery; using the system to continuously monitor pressure on the protective barrier formed by the transducer element in front of the area of the patient prone to nerve damage positional injury during surgery with the site sensor and monitor; and causing an alarm to be actuated to alert medical personnel of a pressure condition when monitored pressure is greater than a predetermined threshold.

In another example, U.S. Pat. No. 7,214,197 discloses an intraoperative neurophysiological monitoring system includes an adaptive threshold detection circuit adapted for use in monitoring with a plurality of electrodes placed in muscles which are enervated by a selected nerve and muscles not enervated by the nerve. Nerve monitoring controller algorithms permit the rapid and reliable discrimination between non-repetitive electromyographic (EMG) events repetitive EMG events, thus allowing the surgeon to evaluate whether nerve fatigue is rendering the monitoring results less reliable and whether anesthesia is wearing off. The intraoperative monitoring system is designed as a "surgeon's monitor," and does not require a neurophysiologist or technician to be in attendance during surgery. The advanced features of the intraoperative monitoring system will greatly assist neurophysiological research toward the general advancement of the field intraoperative EMG monitoring through post-surgical analysis. The intraoperative monitoring system is preferably modular, in order to allow for differential system pricing and upgrading as well as to allow for advances in computer technology; modularity can also aid in execution of the design.

In another example, U.S. Pat. No. 7,006,863 discloses a method and an apparatus for simultaneously assessing the functional status of component parts of the nervous system by presenting sparse stimuli to one or more parts of the sensory nervous system. Sparse stimuli consist of temporal sequences of stimulus conditions presented against a baseline null stimulus condition, where the non-null stimulus condition, or conditions, are presented relatively infrequently. The low probability of encountering a stimulus differing from a baseline or null stimulus condition in sparse stimulus sequences insures that gain control mechanisms within the nervous system will increase the neural response magnitude and also bias the measured responses to those neurone populations having such gain controls. The consequently increased response amplitudes ensure more reliably recorded responses than are obtained with non-sparse stimuli.

In another example, U.S. Patent Application No. 2010/0145222 discloses a nerve monitoring system [that] facilitates monitoring an integrity of a nerve.

In another example, Medtronic discloses its NIM-Response® 3.0 nerve monitoring system, an innovative, intraoperative nerve integrity monitor enabling surgeons to identify and confirm motor nerve function and monitor major motor nerves by monitoring electromyographical (EMG) activity from multiple muscles during minimally invasive or traditional open surgeries and in response to a change in nerve function, providing visual and/or audible alerts. This system also implements artifact detection software for reducing noise and real-time continuous nerve monitoring with its APS™ Electrode.

There have also been attempts to combine the technology of dissection devices with nerve monitoring technology. For example, U.S. Pat. No. 8,050,769 discloses systems and methods for determining nerve proximity, nerve direction, and pathology relative to a surgical instrument based on an identified relationship between neuromuscular responses and the stimulation signal that caused the neuromuscular responses.

In another example, U.S. Pat. No. 5,928,158 discloses an improved surgical instrument which is used for cutting of tissue. The instrument includes a sensor which identifies nerves within the patient which are proximate to the cutting member of the instrument. The entire assembly is hand held and includes both a surgical cutter such as a scalpel blade, scissors, or laser scalpel, as well as the electronics to stimulate nerves within the patient. The electronics monitor is positioned near the tip of the instrument to warn the surgeon of a proximate nerve so that the nerves are not inadvertently severed. In one embodiment of this invention, the scissors are incapacitated when a nerve is sensed to prevent an accidental cutting of the nerve.

In another example, U.S. Patent Application No. 2010/0198099 discloses a signal processing module includes an input module electronically coupled to a sensing probe of a nerve integrity monitoring system. The probe senses electrical signals from a patient during operation of an electrosurgical unit. The input module receives an input signal from the probe. An EMG detection module is coupled to the input module and is adapted to detect conditions in the input signal. The conditions are classified as a function of a level of electromyographic activity. An output module, coupled to the EMG detection module, provides an indication of electromyographic activity in the input signal based on the detected conditions.

In another example, U.S. Patent Application No. 2014/0267243 discloses a surgical scalpel, scalpel instrument and/or scalpel system (collectively, scalpel), particularly designed for use in a transverse carpal ligament surgical procedure, that evaluates an incision path with respect to a nerve in the incision path, and is used to perform the incision if appropriate. The scalpel emits an evaluation signal through a potential incision path through tissue captured by the scalpel. The scalpel utilizes the emitted evaluation signal to determine the presence of a nerve in the incision path. The dissection and evaluation (surgical) instrument includes a blade that is retractable relative to a target tissue capture area thereof. Evaluation may include determining the presence of a nerve before incision and/or the evaluating whether the target tissue has been appropriately captured. A warning is provided when the evaluation determines that a nerve is in the incision path and/or when the captured target tissue is determined to be inappropriate. Alternatively, the surgical instrument may disable extension of the blade when the evaluation determines that a nerve is in the dissection path and/or when the captured target tissue is determined to be inappropriate.

Therefore, there remains an unmet need for the system and method of the invention of the present application that operatively connects nerve monitoring technology and energy based dissection technology to provide a device that provides energy based dissection functionality wherein said energy based dissection technology cannot operate, or operates differently, upon receipt of real time information from the nerve monitoring functionality that nerve damage may be imminent in the absence of such safety shutdown and removing human error and reaction time issues which prevents unintended dissection and concomitant nerve damage. There also exists an unmet need to map out in real time the relative locations of a nerve at risk and an energy based dissection device.

SUMMARY

The present invention provides a solution to the unmet need, by providing an apparatus comprising:

a. a connection to: (i) an energy source capable of powering the apparatus; (ii) an energy based dissection device; and (iii) a nerve integrity monitoring device; and b. a communication link between:
  i. said energy based dissection device; and
  ii. said nerve integrity monitoring device wherein said nerve integrity monitoring device is capable of monitoring the integrity of a given nerve;
  iii. wherein said communication link is capable of receiving information supplied by said nerve integrity monitoring device and transmitting information to the energy based dissection device; performing the steps of:
   1. receiving information from said nerve integrity monitoring device;
   2. interpreting said information;
   3. upon determining a nerve integrity reading that indicates that nerve integrity will likely be compromised by continued operation of the energy based dissection device;
   4. transmitting a functional control command to said energy based dissection device.

In accordance with an embodiment, a nerve mapping system includes an energy based dissection device, a plurality of beacons, and a processing device. The plurality of beacons are disposed in a tissue of a patient. Each beacon is adapted to transmit one or more first electrical signals within the body and receive one or more second energy signals. The processing device is adapted to determine first locations associated with the plurality of beacons, a second location associated with the energy based dissection device, and a third location associated with a nerve within the tissue, based on the one or more second signals, generate a mapping of the first locations, second location, and third location, and cause the first locations, second location, and third location to be displayed on a display device.

In one embodiment, the one or more second energy signals received by a respective beacon include electrical signals generated by a second beacon.

In another embodiment, the one or more second energy signals further include second electrical signals emitted by the energy based dissection device.

In another embodiment, each of the plurality of beacons comprises a wired device. In another embodiment, each of the plurality of beacons comprises a wireless device. In another embodiment, the processor includes one of a personal computer, a laptop device, and a smart phone. In another embodiment, each of the plurality of beacons comprises a transmitter. In another embodiment, each of the plurality of beacons is adapted to be attached to the tissue.

In another embodiment, the energy based dissection device is configured to emit an energy burst for a predetermined time, at a predetermined frequency and at a predetermined power level, the energy burst being sufficient in frequency and power level to be detected by one or more of the plurality of beacons but insufficient in frequency and power level to damage tissue. In another embodiment, the system also includes a manual override to the shutoff command.

In accordance with another embodiment, a system for mapping a nerve is provided. The system includes a surgical device adapted to transmit an energy signal within a tissue of a patient, and a plurality of beacons disposed in the tissue, each of the plurality of beacons including a transmitter and a receiver. Each of the plurality of beacons is adapted to transmit one or more first electrical signals within the tissue at a respective frequency unique to the respective beacon and receive one or more second energy signals. The system also includes a processing device configured to determine first locations associated with the plurality of beacons, a second location associated with the energy based dissection device, and a third location associated with a nerve within the tissue, based on the one or more second signals, and cause a graphical representation of the first locations, second location, and third location to be displayed on a display device.

There are many alternative embodiments to the device of the present invention described elsewhere herein.

It will be appreciated by one of skill in the art the many applications of the device of the present invention and should not be limited by the examples presented herein. For example, and not by way of limitation, any type of energy utilized in dissection may be suitable for use with the device of the present invention. Similarly, any type of nerve or other tissue capable of its integrity being monitored through basic electrode conduction may be suitable for use with the present invention.

BRIEF DESCRIPTION OF THE DRAWINGS

FIG. 11 shows a nerve mapping system in accordance with another embodiment.

DETAILED DESCRIPTION

Figure 1:
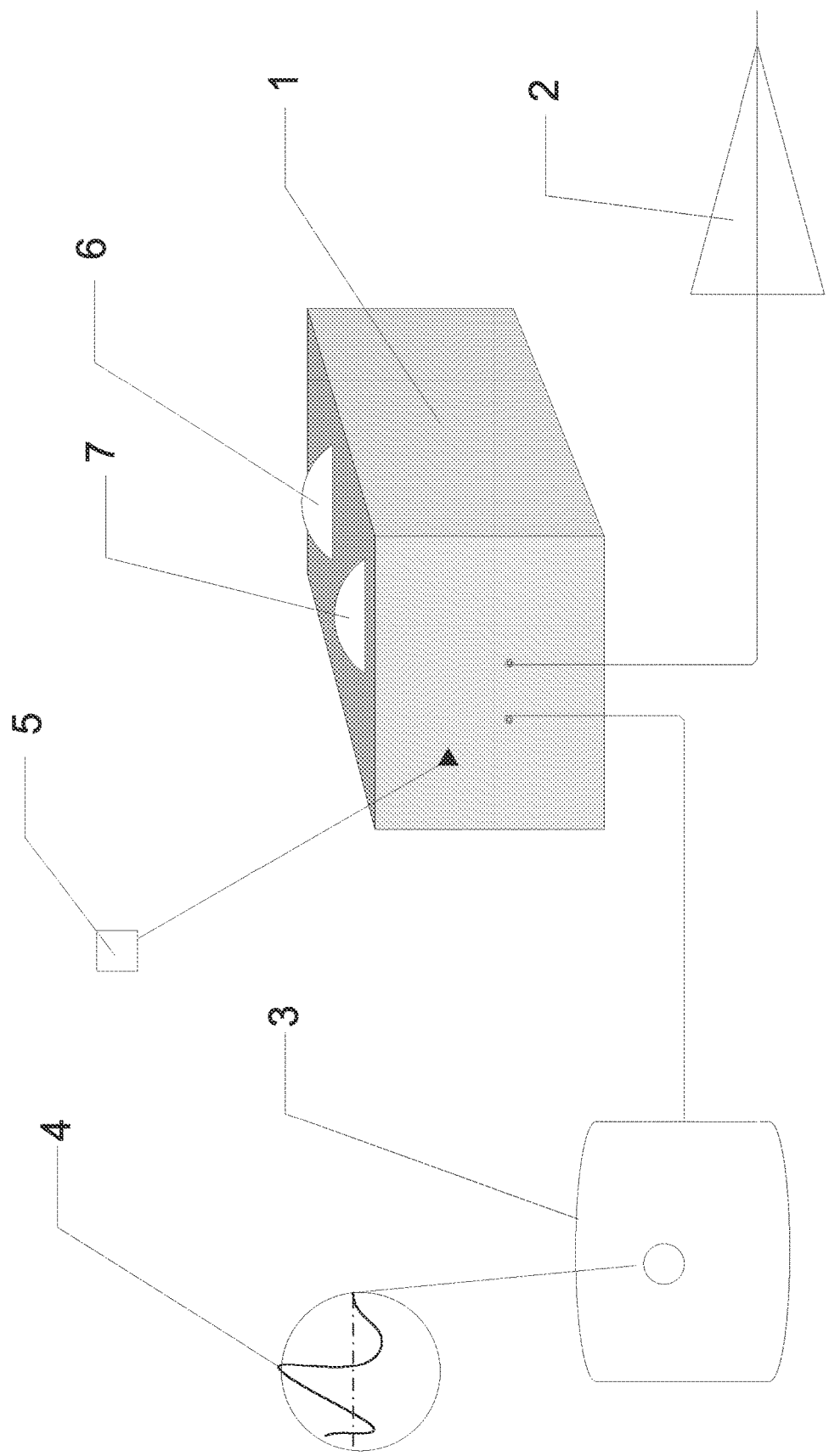
FIG. 1 shows one embodiment of the present invention. The central unit (1) receives an input of energy from an energy source (5) to power all functionality by powering on the central unit with switch (6). After powering on, the central unit (1) supplies power to the nerve monitoring device (3) and the energy based dissection device (2). The nerve monitoring device (3) is connected to the patient (not shown) according to its normal procedure and provides readouts (4) indicating nerve integrity. The central unit (1) also receives information regarding nerve integrity and may adjust or shut off power to the energy based dissection device (2) according to its programming. The central unit (1) may also provide an override switch (7) in order that a surgeon has ultimate decision authority as to energy flow to the energy based dissection device (2).

For clarity of disclosure, and not by way of limitation, the detailed description of the invention is divided into the following subsections that describe or illustrate certain features, embodiments or applications of the present invention.

Definitions

An "energy based dissection device" as used herein refers to any device capable of converting an energy supply into a tool useful for creating a surgical incision or any type of tissue division or separation.

An "energy supply" is any form of energy, capable of, and suitable for, delivering a surgical incision.

A "nerve integrity monitoring device" as used herein refers to any device capable of monitoring nerve integrity.

"Nerve integrity" as used herein refers to maintaining the normal functioning of, within accepted medical tolerance limits, nerve impulse transmission pathways.

A "beacon" is an appropriate energy pulse generator and/or receptor capable of, in certain embodiments, either or both generating and receiving energy pulses. In certain embodiments, they may also be capable of receiving reflections of energy pulses and/or monitoring characteristics of said pulses.

The System of the Present Invention

In one embodiment the present invention provides an apparatus comprising:
a. a connection to: (i) an energy source capable of powering the apparatus; (ii) an energy based dissection device; and (iii) a nerve integrity monitoring device; and
b. a communication link between:
  i. said energy based dissection device; and
  ii. said nerve integrity monitoring device wherein said nerve integrity monitoring device is capable of monitoring the integrity of a given nerve;
  iii. wherein said communication link is capable of receiving information supplied by said nerve integrity monitoring device and transmitting information to the energy based dissection device; performing the steps of:
    1. receiving information from said nerve integrity monitoring device;
    2. interpreting said information;
    3. upon determining a nerve integrity reading that indicates that nerve integrity will likely be compromised by continued operation of the energy based dissection device;

4. transmitting a functional control command to said energy based dissection device.

In one embodiment, the present invention would not be merely a connecting apparatus but would incorporate some or all components into one unified device.

In one embodiment, the nerve integrity monitoring device would be combined with the energy based dissection device such that the nerve integrity monitoring device sensors would be encased within, and at or near the cutting member of, the energy based dissection device.

In one embodiment, the functional control command that would be sent to the energy based dissection device in response to obtaining a nerve integrity reading that nerve integrity is likely to be compromised by continued operation of the energy based dissection device is a shutoff command.

In one embodiment, a shutoff command would have a manual user override.

In one embodiment, a manual user override would be housed on the apparatus. In another embodiment, a manual user override would be housed directly on the energy based dissection device and/or in close proximity to all other normally utilized surgical controls of the energy based dissection device.

In one embodiment, a shutoff command would be of a predetermined length of time. Such length of time would be operator-adjustable. Alternatively, once a shutoff command is transmitted, an affirmative signal to enable energy flow restoration to the energy based dissection device must be manually given by the user.

In one embodiment, the functional control command that would be sent to the energy based dissection device in response to obtaining a nerve integrity reading that nerve integrity is likely to be compromised by continued operation of the energy based dissection device is a reduction of energy to slow the dissection of the energy based dissection device.

In one embodiment, a reduction of energy command would have a manual user override.

In one embodiment, a manual user override would be housed on the apparatus. In another embodiment, a manual user override would be housed directly on the energy based dissection device and/or in close proximity to all other normally utilized surgical controls of the energy based dissection device.

In one embodiment, a reduction of energy command would be of a predetermined length of time. Such length of time would be operator adjustable. Alternatively, once a reduction of energy command is transmitted, an affirmative signal to enable full energy flow restoration to the energy based dissection device must be manually given by the user.

In one embodiment, the nerve integrity monitoring device would perform exactly as it does without the apparatus, i.e., sending normal visual and/or auditory and/or tactile signals to the user irrespective of signals that would be sent to the apparatus.

In one embodiment, the device of the present invention would have a baseline establishment function, wherein the operator could completely remove any operation of the energy based dissection device thereby establishing beyond doubt that there could be no effect of the energy based dissection device on nerve function or integrity and then pressing a reset button or other similar reset functionality to establish a new baseline readout from the nerve integrity monitoring device.

In one embodiment, the device of the present invention would have controls to adjust detection sensitivity threshold based on initial baseline parameters.

In one embodiment, the device of the present invention would provide a test pulse function, wherein the operator would be able to deliver a short duration lower energy burst from the energy based dissection device to an area where it may be thought to be at risk to test the area and review any change in readout from the nerve integrity monitor device prior to delivering a full energy cutting function. Such functionality could be implemented by including an energy dial to reduce the energy delivered to the energy based dissection device or a button that would automatically deliver a predetermined lower energy burst for a predetermined time period through the energy based dissection device before restoring the energy to normal power. The test pulse would be operator adjustable for energy strength and time of duration.

In one embodiment, the device of the present invention would have all functionality switches and buttons allowing operator chosen commands to be placed on the floor to be operated by foot allowing the operator full hand availability for operating procedures. Such foot controls could be hard wired or connected wirelessly to the device of the present invention.

Energy based dissection devices have become commonplace in the modern operating room as a result of their improved efficiencies and precision.

For example, Medtronic provides the PlasmaBlade™ which are a family of disposable cutting and coagulation devices that offer the exacting control of a scalpel and bleeding control of traditional electrosurgery without extensive collateral damage. The PlasmaBlade™ is based on pulsed plasma technology which represents an advancement of radiofrequency surgical technologies.

In another example, Covidien provides the Sonicision™, a cordless ultrasonic dissection device. Covidien advertises that its Sonicision™ device results in "faster dissection than the Harmonic™" device (referring to the Ethicon Harmonic Ace™ device referenced elsewhere herein).

In another example, Covidien provides a portfolio of energy based dissection devices under the ForceTriad™, Valleylab™ and LigaSure™ brands employing a variety of technology including monopolar and bipolar electrosurgery components.

Generally, electrosurgery refers to the cutting and coagulation of tissue using high-frequency electrical current. Electrical current is created by the movement of electrons and voltage is the force that creates this movement. There are two types of electrical current—direct current (DC), where the electrons always flow in the same direction, and alternating current (AC), where the current changes direction periodically. With AC, each time the current reverses, it is considered one cycle. Frequency refers to the number of cycles in one second and is measured in hertz (Hz).

Basic electrosurgery units used in operating rooms convert standard AC frequencies, i.e., 50 Hz to 60 Hz as delivered from a typical wall outlet to much higher frequencies such as from 500,000 Hz to 3,000,000 Hz. This is necessary to minimize nerve and muscle stimulation, which occurs at frequencies below 10,000 Hz.

Basic electrosurgery units are subject to electromagnetic interference, either interruption of their normal operating parameters by other instruments generating a nearby electrical field or interfering with the normal operation of other nearby instruments.

Certain non-electrical energy based dissection devices may overcome this interference. Examples include, but are not limited to, ultrasonic energy based dissection devices and thermal energy based dissection devices.

All of these devices have some type of thermal and/or electrical spread, i.e., the surgeon intends to cut through a specific tissue and at least a minimal amount of adjacent tissue is affected. The key is to minimize the spread so that a minimal amount of adjacent tissue is affected with unintended consequence. Of significant importance is when such adjacent tissue is nerve tissue.

Another consideration is interference with intra-operative monitoring equipment. Responses have included functionality that includes argon beam coagulation, lasers, ultrasound, saline enhancement and ferromagnetic technology for minimizing the need for actual electric current passing through tissue.

Nerve integrity monitoring devices have also become commonplace in the modern operating room where certain surgeries place at risk damage to significant nerve tissues.

For example, Medtronic's NIM-Neuro® 3.0 nerve integrity monitoring system provides an eight-channel nerve monitoring system delivering advanced monitoring features such as simultaneous monitoring during bipolar cautery, real-time continuous monitoring with an APS™ electrode, artifact detection software to help reduce noise, signal overlay in a microscope, use of two stimulators at one time, touchscreen operation, and audio and visual alerts.

In another example, Natus® Neurology provides the XLTEK Protektor 32™ IOM system with multimodality monitoring, configurable stimulus interleaving, nerve integrity monitoring mode to identify neural structures and confirm efferent nerve function and selectable stimulator contact chimes.

In another example, NuVasive™ provides its NVM5® nerve monitoring system for real-time, precise and reliable feedback to ensure nerve and spinal cord safety. By using this unique and advanced technology, the surgeon is provided with intraoperative information about the location and function of the nerves.

In all of the foregoing examples, the surgeon is provided information, either in the form of an audible or visual signal or some type of wave readout that must be first received and then understood prior to the surgeon reacting. Thus, there is room for surgeon error in interpretation as well as reaction time issues in utilizing the existing nerve monitoring technology.

In one embodiment, the device of the instant invention provides an apparatus wherein any one of the foregoing examples of energy based dissection devices or some other equally suitable energy based dissection device is connected to the apparatus such that the apparatus delivers, with the capability to control, the flow of energy to the energy based dissection device. Alternatively, the energy based dissection device may be powered separately and the apparatus is merely capable of interrupting and/or altering the flow of energy to the energy based dissection device.

In one embodiment, the device of the instant invention provides an apparatus wherein any one of the foregoing examples of nerve integrity monitoring devices or some other equally suitable nerve integrity monitoring device is connected to the apparatus such that the apparatus is capable of receiving information from the nerve integrity monitoring device. The apparatus may power the nerve integrity monitoring device or the nerve integrity monitoring device may be powered separately.

In one embodiment, the device of the instant invention provides an apparatus which, upon receiving information from the nerve integrity monitoring device, is capable of interpreting the information received to determine if nerve integrity is likely to be compromised by continued exposure to levels of energy that triggered the reading in the first instance.

In one embodiment, the device of the instant invention provides an apparatus that upon interpreting information that nerve integrity is likely to be compromised, is capable of delivering an appropriate command to the energy based dissection device. An appropriate command may be one that simply shuts off energy to the energy based dissection device. Another appropriate command may be one that reduces the flow of energy to the energy based dissection device.

Nerve integrity monitoring devices typically provide functionality by providing electrodes that are in functional contact with a nerve to be monitored. The nerve integrity monitoring devices can then detect whether the nerve at issue is functioning normally and providing an unbroken circuit or if the nerve has been damaged and cannot complete the circuit normally.

Figure 2:
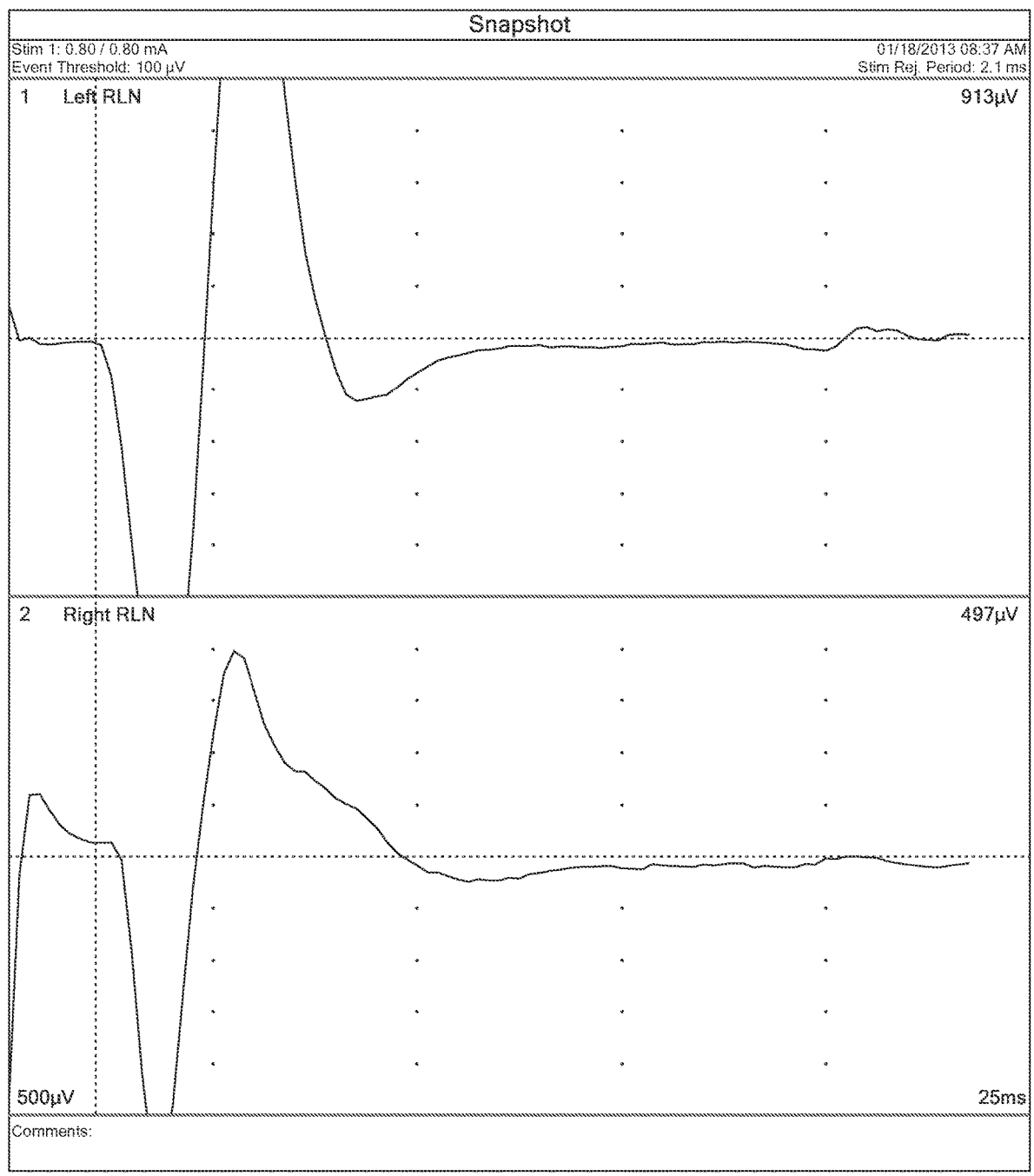
FIG. 2 shows one potential readout of a nerve monitoring device in response to monitoring of a laryngeal nerve during surgery.

In FIG. 2, the wave readouts demonstrate that the nerve at issue (in this case a recurrent laryngeal nerve ("RLN") which is at risk in thyroid, parathyroid and other surgeries performed close to the course of the RLN) is functioning as expected when an external stimulus is present.

Figure 3:
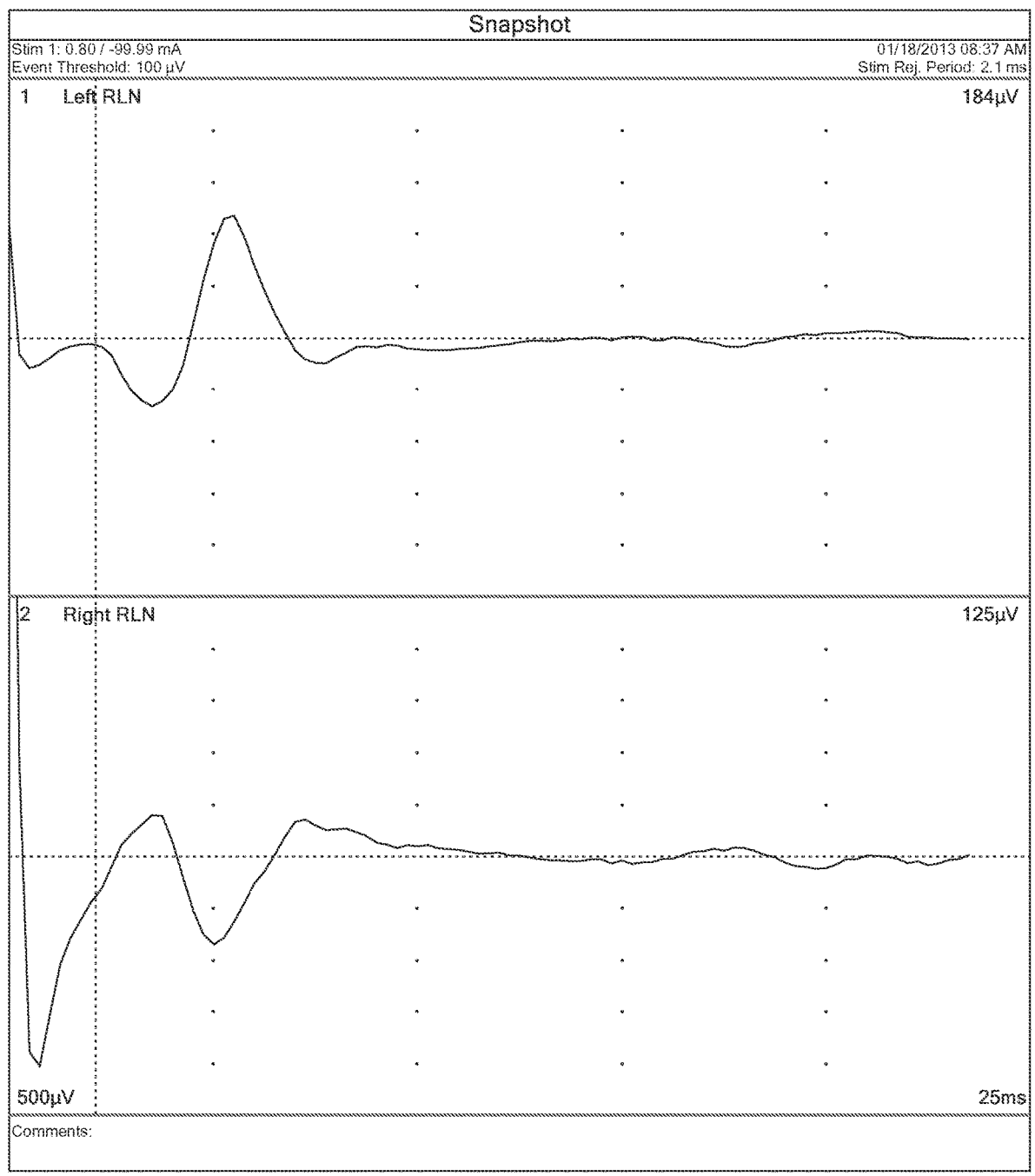
FIG. 3 shows another potential readout of a nerve monitoring device in response to monitoring of a laryngeal nerve during surgery.

In FIG. 3, the wave readouts (again, in the case of an RLN) similarly demonstrate expected functionality. The differences between FIGS. 2 and 3 reflect the differences in stimuli, the actual proximity to the RLN (i.e, direct contact versus immediate proximity), the specific location along the RLN that the stimulus occurs, and the like.

Figure 4:
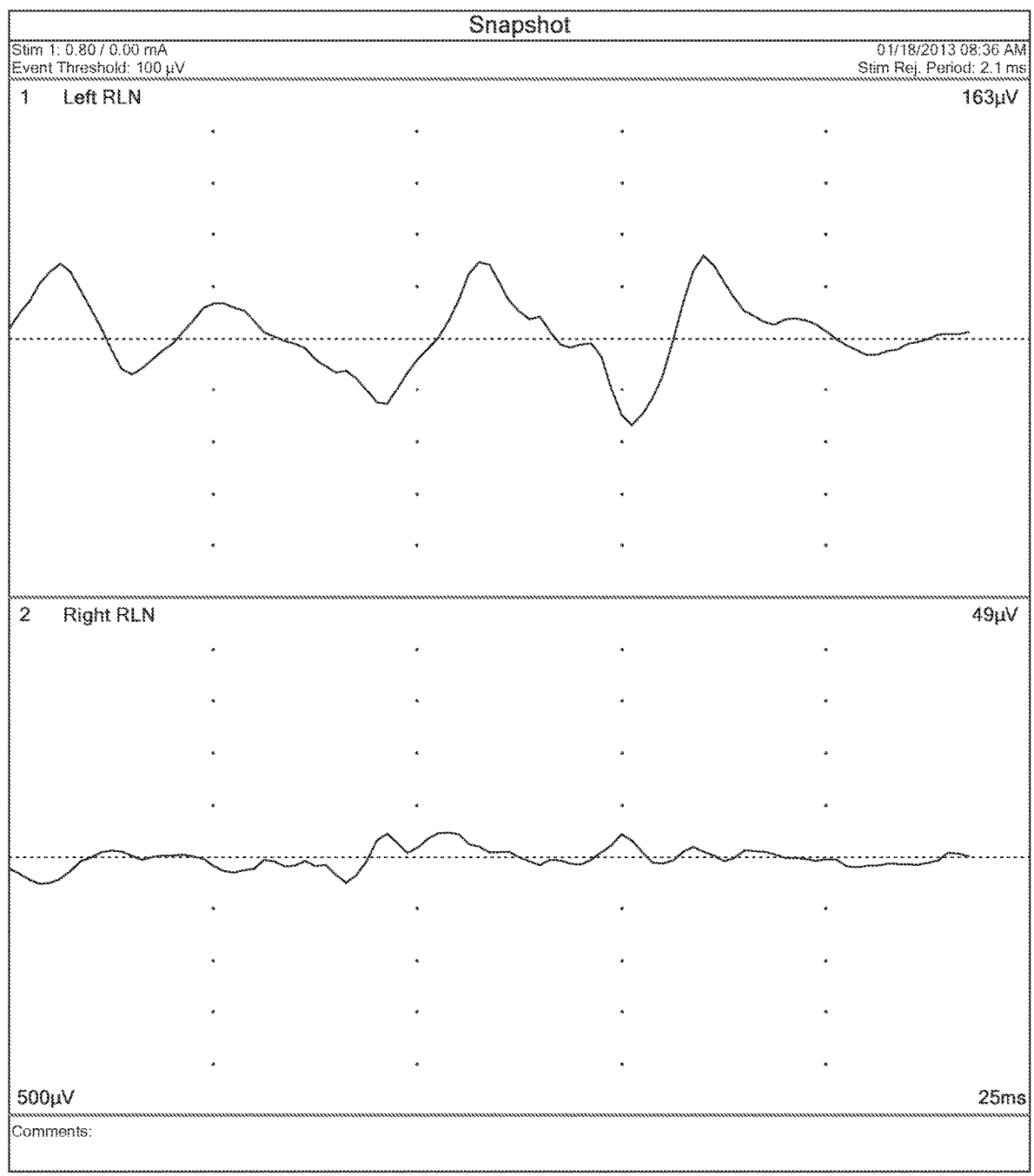
FIG. 4 shows another potential readout of a nerve monitoring device in response to monitoring of a laryngeal nerve during surgery.

In FIG. 4, the wave readouts (again, in the case of an RLN) demonstrate an RLN that is experiencing nearby or indirect stimulus (traction and/or physical trauma).

Figure 5:
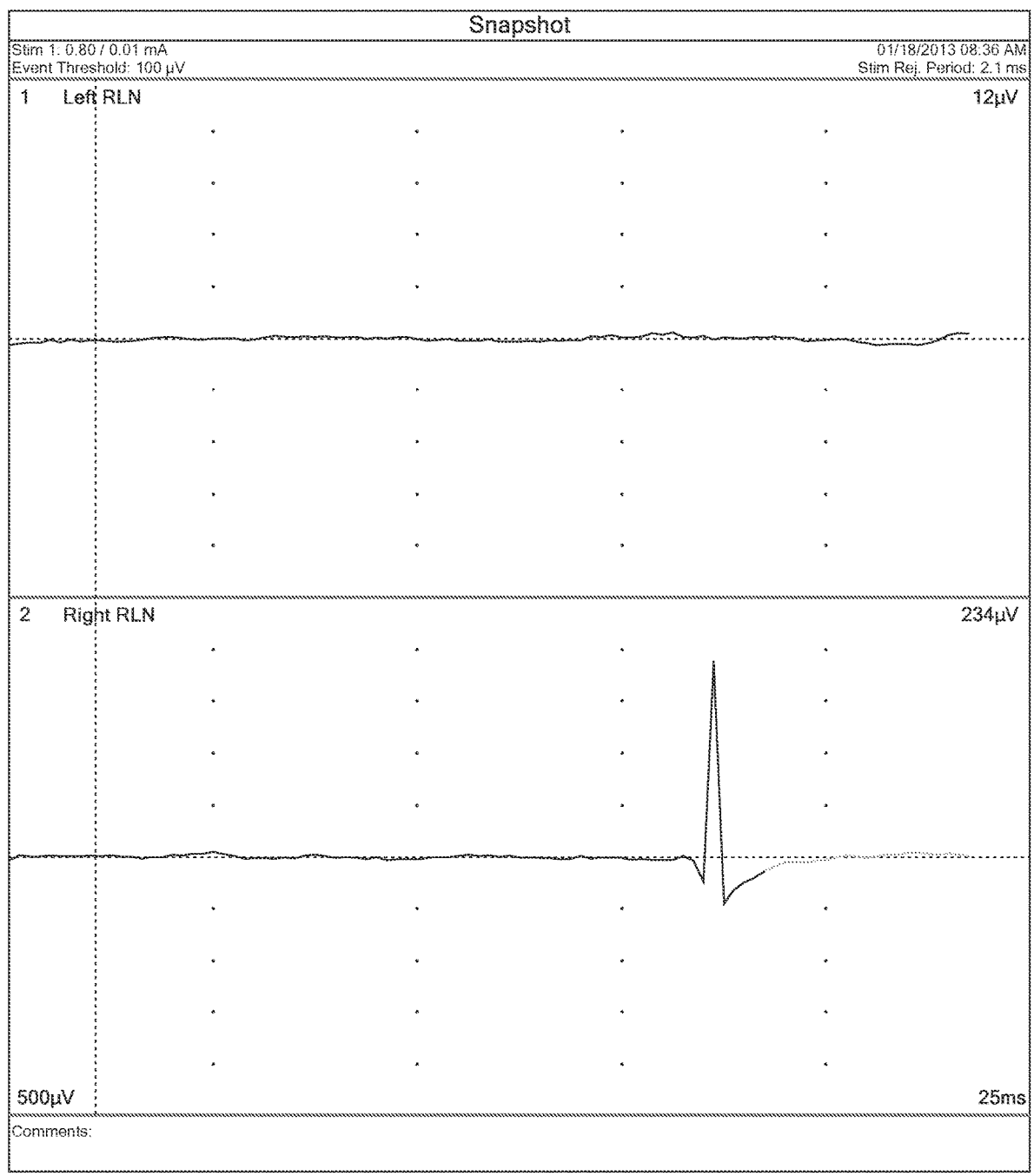
FIG. 5 shows another potential readout of a nerve monitoring device in response to monitoring of a laryngeal nerve during surgery.
Figure 6:
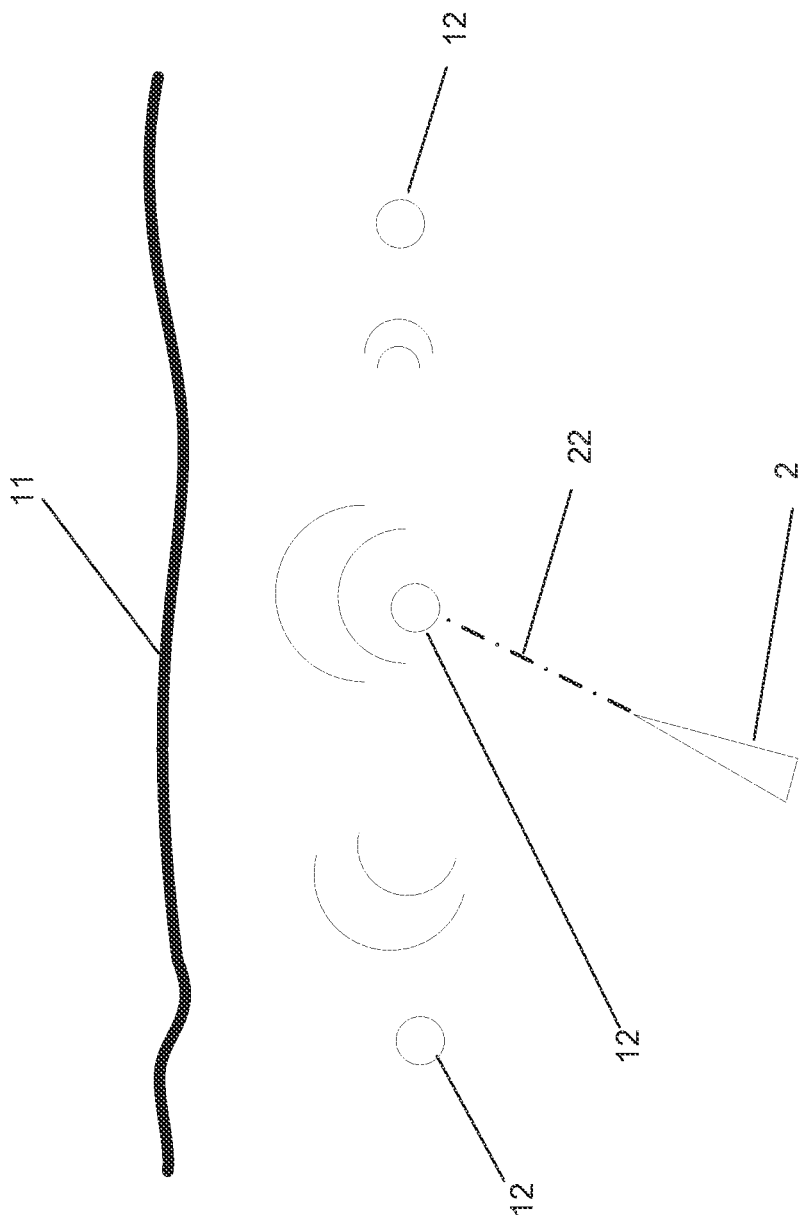
FIG. 6 shows an alternative embodiment of the device of the present invention wherein external beacons (12) are placed in proximity to the nerve to be monitored (11) wherein said beacons (12) are capable of monitoring emissions of energy pulses (22) from the energy based dissection device (2) and reflections thereof.

In FIG. 5, (again, in the case of an RLN), the top wave readout indicates an RLN that is undisturbed, while the bottom wave readout indicates an RLN that is undisturbed for a period of time and then indicates a stimulus of expected RLN functionality.

Reference to the foregoing figures demonstrate that a variety of wave readouts are possible based upon many factors such as the actual nerve to be monitored, the strength of the energy wave of the energy based dissection device, the method of monitoring nerve integrity and actual proximity to the nerve of the energy based dissection device when an energy pulse is delivered.

One of skill in the art will appreciate that where all other variables are constant and/or predetermined and accurately measured and controlled, the actual and/or relative proximity to the nerve to be monitored may be determined by interpreting the nerve monitoring device wave readouts.

This nerve proximity monitoring function can be implemented to create a nerve mapping function based on interpreting data gathered simultaneously from multiple electrodes at various points along a particular nerve, and/or from mathematical vector analysis of the nerve monitoring waveform resulting from single or multiple energy stimuli.

Each time a nerve senses an electrical impulse, it reacts in a way that provides a specific wave readout in the nerve monitoring device. As noted, these wave readouts can be interpreted to provide a shutoff command to the energy based dissection device when such device is so close to the nerve to be monitored that continued supply of energy is likely to damage the nerve integrity. Such readouts can also be used to determine nerve proximity and nerve mapping. By continuously determining such nerve proximity, changes in proximity can be measured and create a vector mapping of nerve location and orientation. By sensing against predetermined areas along a nerve, three dimensional nerve mapping can be accomplished. By plotting this information against known nerve structure, an accurate indication can be determined of likely nerve location, size and orientation in relation to the current location of the energy based dissection device. The more readings that are obtained, the more accurate this nerve location plotting can be.

Inherent in the waveform readouts from a nerve integrity monitoring device are vector data. A vector is a quantity that has both direction and magnitude. Nerves function by conducting energy along its length, i.e., the nerve integrity is measured by the magnitude and direction of such energy conduit. A given nerve is generally known in terms of its size, shape, ability to conduct energy and relative location within any particular patient based on that patient's age, size, condition and other criteria. Based on a library of a multitude of prior readings from subjects similar to a given patient and a baseline reading from the specific patient, mathematical vector analysis on the vector data contained within given waveform readouts can be used to project an accurate real-time mapping of the given nerve relative to the location of the energy based dissection device. As the operator moves the energy based dissection device, the relative distance from it to a given point along the given nerve changes. This new data, also containing vector data, is used to continuously update and refine the relative location of the given nerve to the energy based dissection device. For example, a given nerve of a given size and condition will be expected to generate a waveform of certain characteristics within tolerance limits in response to stimuli of a given energy pulse at a certain distance. Moreover, that nerve will be known to exist generally in size and location within a patient and to conduct energy in a certain direction. The operator can establish a baseline by providing a known energy pulse at a known distance to a specific nerve in an area where such movements and locations can be readily observed. Once these initial readings are established and comport with expected values, then, as the operator moves into the surgery, all waveforms will be analyzed against these known parameters. One of ordinary skill in the art will appreciate that using vector data analysis, an accurate plot of the actual nerve size and location relative to the energy based dissection device can be performed.

In one embodiment, the nerve integrity can be monitored along multiple points of its trajectory, and/or through vector analysis of the waveform. Thus, when the energy based dissection device sends out an energy pulse, multiple wave readouts ensue simultaneously, each bearing specific characteristics, including vector data, based upon the proximity of that particular sensor point to the energy based dissection device. Thus, the plotting of the nerve location and orientation with respect to the energy based dissection device can be even more accurate.

In one embodiment, this nerve location and orientation is plotted in real time on a graphical display on the device of the present invention.

In one embodiment, nerve location and orientation information can be supplemented with information beacons. In one embodiment, beacons capable of delivering energy pulses can be placed in situ into nearby soft tissue and held in place with prongs prior to beginning a surgical procedure. The beacons could be wireless or connected to either the energy based dissection device or the nerve integrity monitoring device or a separate communicatively connected functional apparatus within the device of the present invention with wires. Such beacons would emit a known energy pulse at various known frequencies and duration to be received by the electrodes monitoring nerve integrity. In this manner, the nerve size, location, orientation and integrity can be monitored relative to the beacon pulses prior to any energy pulse generated by the energy based dissection device in all of the same ways as just discussed. Then, when the energy based dissection device is introduced into the equation, the known energy being introduced by said device is compared to the readings obtained by the beacon pulses. In this manner, information will be generated to determine the proximity of the beacons to the nerve and with greater accuracy, the proximity of the energy device to the beacons and thus, the nerve.

In one embodiment, the beacons could also receive energy signals and detect the nerve data independent of and in addition to the nerve integrity monitoring device, and also detect the energy based dissection device. The nerve integrity monitoring device is still needed to monitor actual nerve integrity. However, the additional information gathered from reflected energy pulses between the beacons and the nerve and the energy based dissection device and the beacons will yield greater accuracy of nerve location, size, and orientation.

In accordance with an embodiment, beacons provide a mapping functionality. In particular, the geographic proximity of a nerve at risk, and the energy device (i.e. electrocautery, bipolar cautery, or other), are determined and mapped, and a graphical representation of this geographic relationship is generated and displayed on a screen in real time.

Figure 7:
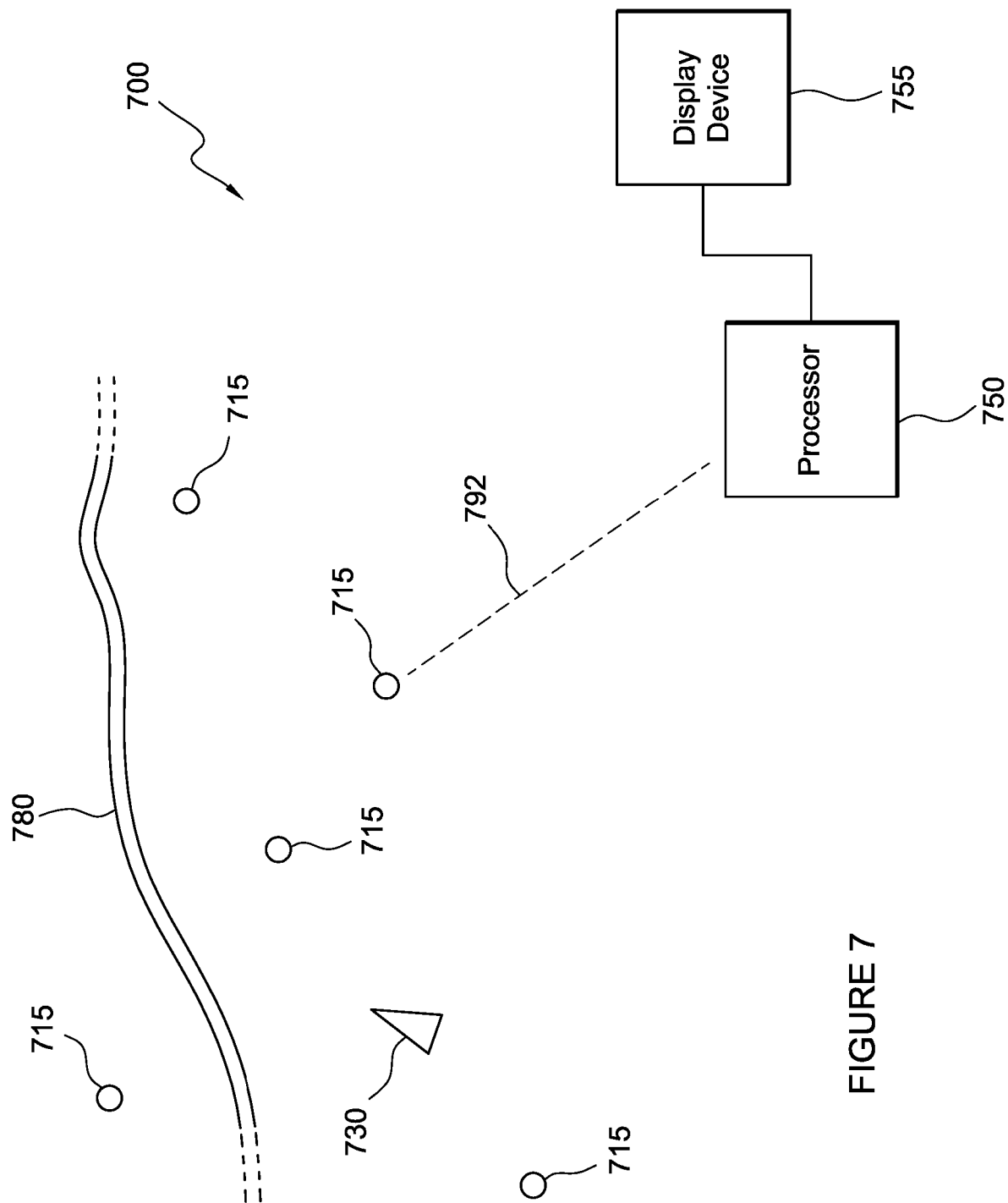
FIG. 7 shows a nerve mapping system in accordance with an embodiment.

FIG. 7 shows a nerve mapping system in accordance with an embodiment. Nerve mapping system 700 includes a plurality of beacons 715, an energy based dissection device 730, a processor 750, and a display device 755. In the illustrative embodiment, beacons 715 are disposed proximate a nerve 780.

In accordance with an embodiment, the beacons include small non-disposable electrical transmitter/receivers. The beacons may be wired devices or wireless devices. A central control panel interfaces with the beacons and controls transmissions/emissions from the beacons.

Beacons 715 are configured to transmit electrical energy or pulses. Beacons 715 may transmit electrical signals as dictated by processor 750. In the illustrative embodiment, communications between a beacon 715 and processor 750 are illustrated by path 792. These signals may be of varying intensity and strength. The signals may also vary in time frequency. The signals may be different from the energy emitted by the energy cutting and cauterizing device. Beacons 715 also have a receive function in which they receive/detect electrical impulses. For example, beacons 715 may detect electrical signals generated by other beacons, electricals signal reflected by tissues (including nerves), and electrical signals reflected by other devices. Individual beacons 715 may emit energy of different strengths, frequency, waveforms, or with other uniquely identifiable characteristics to allow the system to distinguish between different beacons for mapping purposes. For example, a first beacon may transmit signals using a first frequency, a second beacon may transmit signals using a second frequency, etc.

In one embodiment, the beacons 715 may attached to soft tissue. For example, the beacons may have a clockwise twist capability so that they stick to tissue.

In accordance with an embodiment, processor 750 controls the functioning of the beacons, processes, integrates and interprets data from the beacons, and generates a graphical display of the data. Processor 750 and display device 755 may be implemented by, for example, a personal computer, a laptop device, a smart phone, etc. Processor 750 also determines, for each action performed by the beacons, whether or not the action is successful and whether or not the target structures have been successfully detected or identified. The processor notifies the user of progress or failure with respect to each activity.

Figure 8:
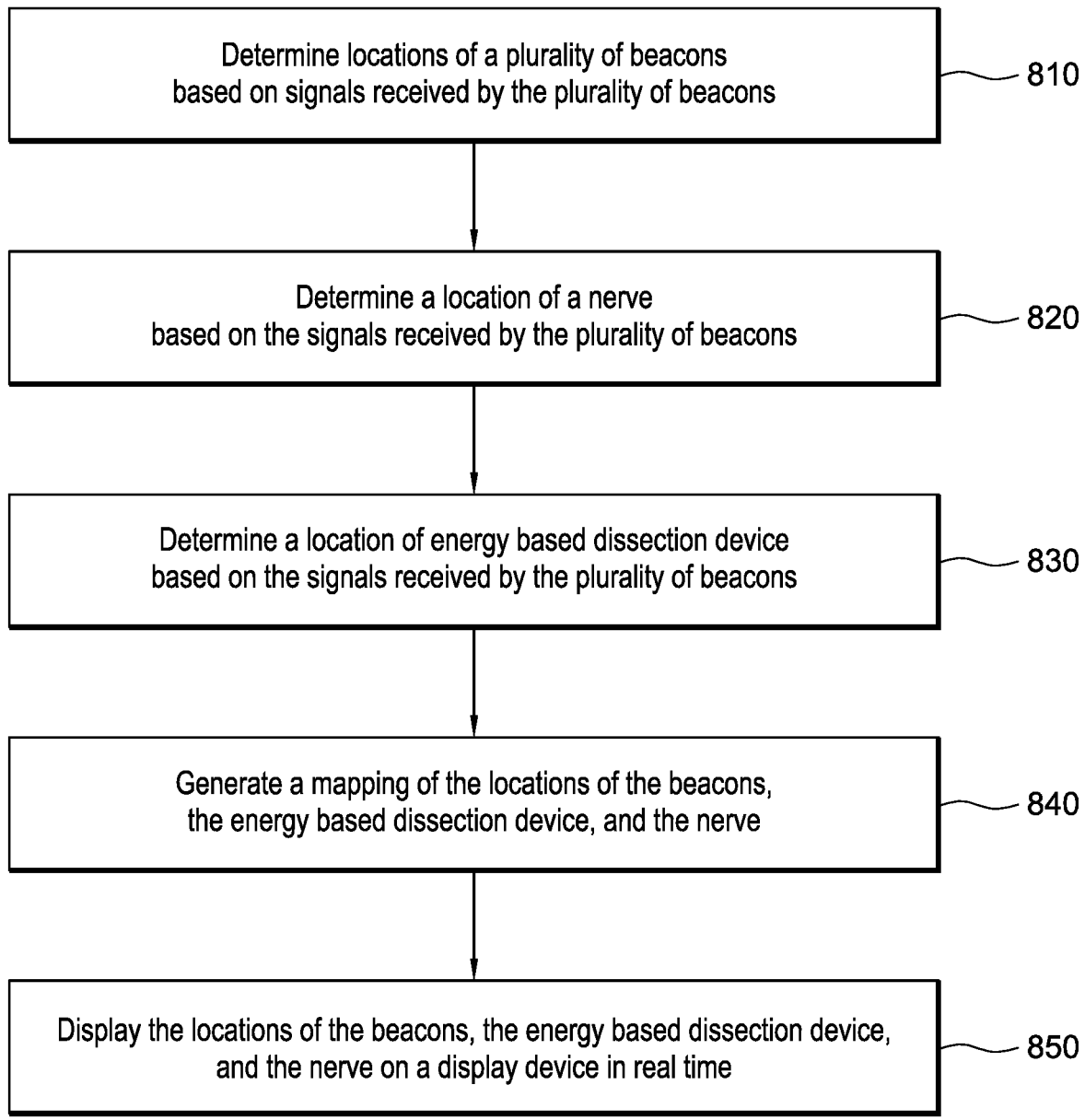
FIG. 8 is a flowchart of a method in accordance with an embodiment.

In accordance with an embodiment, processor 750 analyzes information gathered by beacons 715 and determines the locations of beacons 715, nerve 780, and energy based dissection device 730 based on the information obtained by the beacons. FIG. 8 is a flowchart of a method in accordance with an embodiment.

In the illustrative embodiment, beacons 715 transmit electrical signals and detect electrical signals generated by other beacons, electrical signals reflected by various tissues, and electrical signals reflected by other devices (e.g., other beacons). Beacons 715 also detect energy emitted by energy based dissection device 730.

At step 810, locations of a plurality of beacons are determined based on information obtained by the plurality of beacons. Processor 750 analyzes the electrical signals detected by beacons 715 to determine the locations of the beacons. Specifically, processor 750 may analyze signals such as (1) signals transmitted by a first beacon 715 and received by a second beacon 715, either directly or after reflection, (2) signals transmitted by energy based dissection device 730 and received by a beacon 715, and (3) signals transmitted by a beacon 715 and received by the same beacon after reflection. Based on these signals, processor 750 determines the relative positions of beacons 715 in space within the patient's body. As discussed above, individual beacons 715 may emit energy of different strengths, frequency, waveforms, or with other uniquely identifiable characteristics to allow the system to distinguish between different beacons for mapping purposes. For example, a first beacon may transmit signals using a first frequency, a second beacon may transmit signals using a second frequency, etc. Accordingly, processor 750 may identify individual beacons based on characteristics of their respective signals. Processor 750 may also determine if a particular signal is received directly or after reflection.

At step 820, a location of a nerve is determined based on information obtained by the plurality of beacons. In the illustrative embodiment, processor 750 analyzes the signals detected by beacons 715 to determine the location of nerve 780 relative to the positions of the beacons.

For example, beacons 715 may emit electrical energy that causes the nerve to react. Processor 750 may increase the voltage differentially in the beacons until the nerve reacts. Alternatively, processor 750 may vary the voltage by evaluating the change in the electrical impulse transmission through the soft tissue caused by the nerve and its myelin sheath. For example, the nerve may slow down, block, or deflect the impulses, in ways that the receptor function of the beacon could detect.

At step 830, a location of energy based dissection device 730 is determined based on information obtained by the plurality of beacons. In the illustrative embodiment, processor 750 analyzes the signals detected by beacons 715 (e.g., signals from energy based dissection device 730) and determines the location of energy based dissection device 730 relative to the positions of beacons 715.

At step 840, a mapping of the locations of beacons 715, energy based dissection device 730, and nerve 780 is generated. Processor 750 generates a mapping of the relative positions of beacons 715, energy based dissection device 730, and nerve 780. A mapping may have any suitable form. For example, a mapping may include, for example, a set of three dimensional coordinates associated with the beacons, energy based dissection, and nerve. A mapping may include a set of vectors associated with the beacons, the energy based dissection device, and nerve. Other formats may be used. The mapping may be generated in real-time, for example.

The mapping is also updated in real time. Thus, as information is received from the beacons, processor 750 continually updates the mapping.

Figure 9:
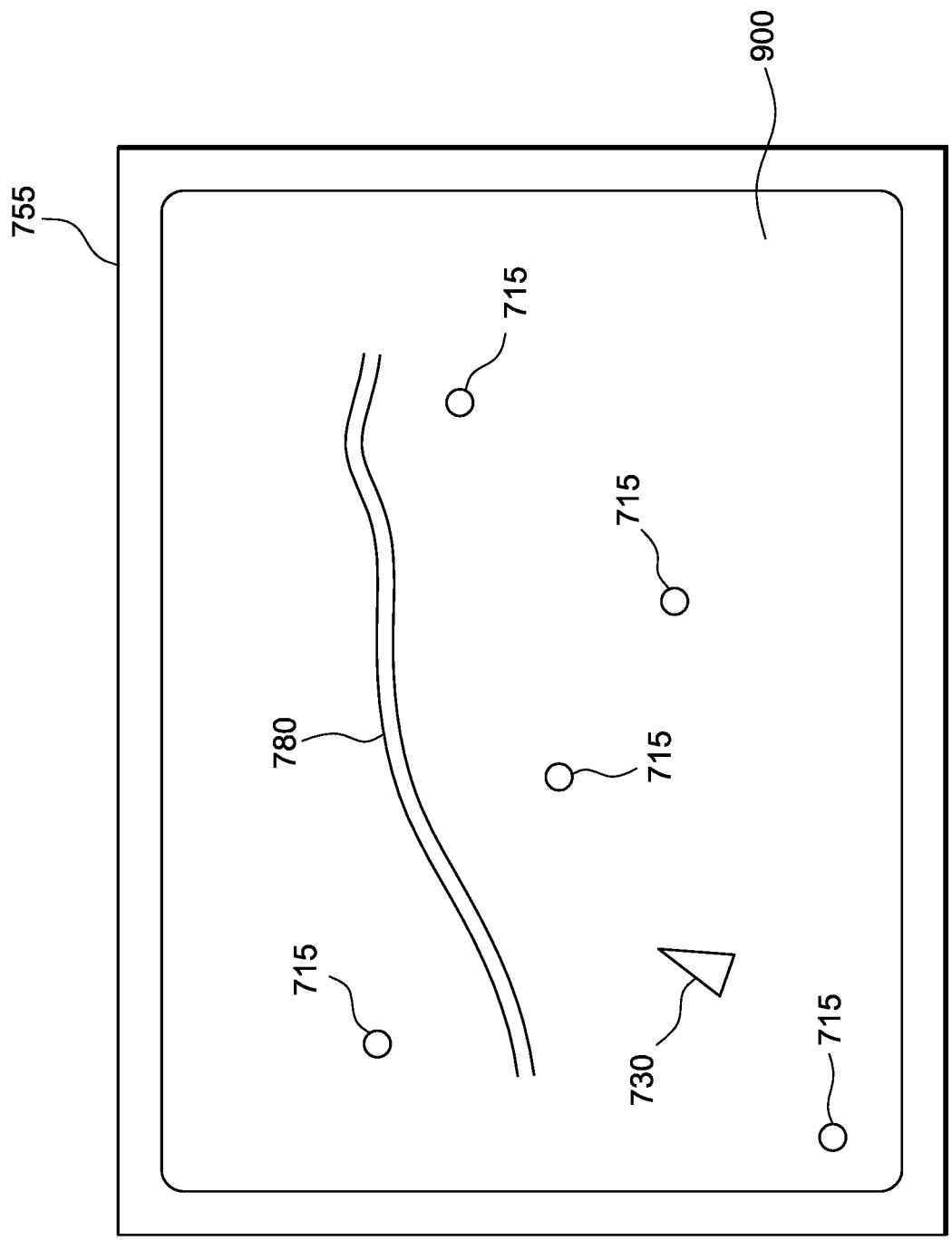
FIG. 9 shows a display of graphical representation a plurality of beacons, an energy based dissection device, and a nerve that may be displayed on a display device in accordance with an embodiment.

At step 850, the locations of beacons 715, energy based dissection device 730, and nerve 780 are displayed on a display device in real time during a surgery. Display device 755 displays a graphical representation of beacons 715, energy based dissection device 730, and nerve 780 based on the mapping. FIG. 9 shows a display 900 of a graphical representation of a plurality of beacons (715), an energy based dissection device (730), and a nerve (780) that may be displayed on a display device (755) in accordance with an embodiment.

In various embodiments, the method steps described herein, including the method steps described in FIG. 8, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 8, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 10:
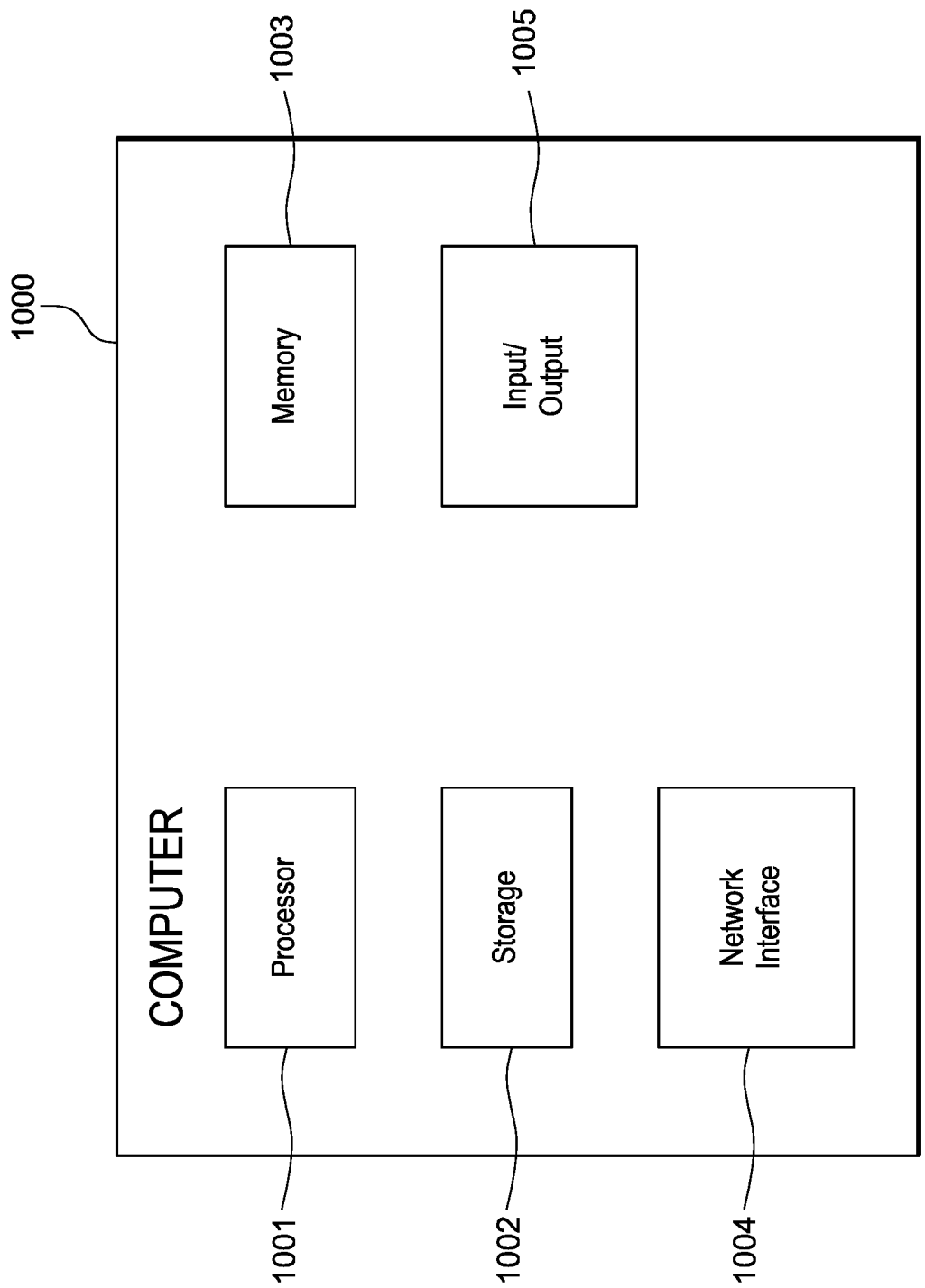
FIG. 10 is a high-level block diagram of an exemplary computer that may be used to implement certain embodiment.

A high-level block diagram of an exemplary computer that may be used to implement systems, apparatus and methods described herein is illustrated in FIG. 10. Computer 1000 includes a processor 1001 operatively coupled to a data storage device 1002 and a memory 1003. Processor 1001 controls the overall operation of computer 1000 by executing computer program instructions that define such operations. The computer program instructions may be stored in data storage device 1002, or other computer readable medium, and loaded into memory 1003 when execution of the computer program instructions is desired. Thus, the method steps of FIG. 8 can be defined by the computer program instructions stored in memory 1003 and/or data storage device 1002 and controlled by the processor 1001 executing the computer program instructions. For example, the computer program instructions can be implemented as computer executable code programmed by one skilled in the art to perform an algorithm defined by the method steps of FIG. 8. Accordingly, by executing the computer program instructions, the processor 1001 executes an algorithm defined by the method steps of FIG. 8. Computer 1000 also includes one or more network interfaces 1004 for communicating with other devices via a network. Computer 1000 also includes one or more input/output devices 1005 that enable user interaction with computer 1000 (e.g., display, keyboard, mouse, speakers, buttons, etc.).

Processor 1001 may include both general and special purpose microprocessors, and may be the sole processor or one of multiple processors of computer 1000. Processor 1001 may include one or more central processing units (CPUs), for example. Processor 1001, data storage device 1002, and/or memory 1003 may include, be supplemented by, or incorporated in, one or more application-specific integrated circuits (ASICs) and/or one or more field programmable gate arrays (FPGAs).

Data storage device 1002 and memory 1003 each include a tangible non-transitory computer readable storage medium. Data storage device 1002, and memory 1003, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices. Data storage device 1002 may also store images and/or other data on detachable storage devices such as a USB drive.

Input/output devices 1005 may include peripherals, such as a printer, scanner, display screen, etc. For example, input/output devices 1005 may include a display device such as a cathode ray tube (CRT) or liquid crystal display (LCD) monitor for displaying information to the user, a keyboard, and a pointing device such as a mouse or a trackball by which the user can provide input to computer 1000.

Any or all of the systems, devices, and apparatus discussed herein, and components thereof, may be implemented using a computer such as computer 1000.

One skilled in the art will recognize that an implementation of an actual computer or computer system may have other structures and may contain other components as well, and that FIG. 10 is a high level representation of some of the components of such a computer for illustrative purposes.

EXAMPLES

For clarity of disclosure, the following examples are based on a typical thyroid surgery procedure that potentially harms the RLN. One of ordinary skill in the art will appreciate the many embodiments of the system of the present invention, for example, and not by way of limitation, back or spinal surgery, surgery proximate to the optic nerve, surgery proximate to the brain stem, and the like.

In a typical thyroid surgery, RLN injury is a dreaded potential complication because surgical cutting devices usually operate in close proximity to the RLN during surgery. With the advance of surgical cutting devices, including the use of energy based dissection devices, the cutting (and other unwanted trauma) can happen in an instant.

Mechanisms of RLN injury may include transection, stretch/traction, crush, ligature entrapment, electrical, thermal, and ischemia.

Factors that increase risk of RLN injury may include re-operation to correct an issue, non-identification of the RLN, inexperience, variances in anatomy, or other unexpected variables such as goiter size and location.

Any device that can minimize these risk factors is desirable.

The early devices and methods aimed at reducing risk include devices to identify and monitor RLN integrity.

For example, use of hook-wire electrodes placed endoscopically into the thyroarytenoid muscles to track ongoing EMG over continuously updated sampling epochs.

In another example, subdermal electrodes are endoscopically placed bilaterally into the posterior cricoarytenoid muscles.

However, there are disadvantages of intramuscular EMG electrode placement such as, such placement is "blind" and subject to dislodgment.

Surface electrodes have been implemented. An example is an electrode consisting of paired silver flexograph plates attached to a polyethylene base, which is curved to conform to the postcricoid area.

Advances now include the use of an EMG endotracheal tube consisting of a low-pressure cuffed silicone elastomer tube with integrated bilateral paired 0.16 inch diameter stainless steel wire electrodes that run in protective channels along the tube and are exposed for 30 millimeters at the glottis lovel and skewed anterolaterally for vocal cord contact and provides for continuous tracking of EMG activity.

Once anesthesia is induced, the endotracheal tube is placed such that the vocal cord is in true contact with the exposed electrodes. Baseline stimulation is recorded to insure identification of the RLN and recognition of an event that causes such stimulation. The surgery is then conducted. After the surgical specimen is removed, the RLN is again stimulated to insure post procedure integrity.

If, during the surgery, the surgeon recognizes a stimulus pattern (such as those indicated in FIGS. 2-4) wave readout from the nerve integrity monitoring device, he knows that he is stimulating the RLN and needs to cease doing whatever it is that he was doing at that moment and re-establish a safe operating pathway.

Other surgical advances include the use of energy based dissection devices, such as those described above. They provide for near instantaneous dissection along a surgical path. The danger is that if that surgical path erroneously is an unsafe operating pathway, damage can be done to the RLN prior to the ability of the surgeon to recognize a stimulus pattern (such as those indicated in FIGS. 2-4) that indicates inadvertent stimulus resulting in damage to the RLN.

The device of the present invention provides a way to eliminate surgeon reaction time and surgeon error in recognition by providing a device that receives the wave readout information in real time and simultaneously interprets such wave readouts and upon interpreting a readout that indicates any potential damage to the RLN, cuts power to the energy based dissection device such that even if the surgeon does not have time to react, the RLN will cease being stimulated.

This will give time to the surgeon to consider his pathway, identify potential damage, and restart the procedure prior to any damage to the RLN occurring.

Accordingly, in accordance with an embodiment, a nerve mapping system includes an energy based dissection device, a plurality of beacons, and a processing device. The plurality of beacons are disposed in a tissue of a patient. Each beacon is adapted to transmit one or more first electrical signals within the body and receive one or more second energy signals. The processing device is adapted to determine first locations associated with the plurality of beacons, a second location associated with the energy based dissection device, and a third location associated with a nerve within the tissue, based on the one or more second signals, generate a mapping of the first locations, second location, and third location, and cause the first locations, second location, and third location to be displayed on a display device.

Systems, methods, and apparatus described herein are not limited to use with an energy based dissection device, but may be used with other types of surgical devices, including scalpels, scissor, etc. Thus, in accordance with another embodiment, a system for mapping a nerve is provided. The system includes a surgical device adapted to transmit an energy signal within a tissue of a patient, and a plurality of beacons disposed in the tissue, each of the plurality of beacons including a transmitter and a receiver. Each of the plurality of beacons is adapted to transmit one or more first electrical signals within the tissue at a respective frequency unique to the respective beacon and receive one or more second energy signals. The system also includes a processing device configured to determine first locations associated with the plurality of beacons, a second location associated with the energy based dissection device, and a third location associated with a nerve within the tissue, based on the one or more second signals, and cause a graphical representation of the first locations, second location, and third location to be displayed on a display device.

FIG. 11 shows a nerve mapping system in accordance with another embodiment. Nerve mapping system 1100 includes a plurality of beacons 1115 and a surgical instrument 1130, which may be an energy based dissection device, for example, or may be a scalpel, scissors, etc. System 1100 also includes a processor 1150 and a display device 1155. Processor 1150 communicates with beacons 1115, for example, via path 1192. Each beacon 1115 may communicate with processor 1150 wirelessly, or by wired connection. In the illustrative embodiment, beacons 1115 are disposed in a patient's tissue proximate a nerve 1180. The components of system 1100 function in a manner similar to those of system 700 shown in FIG. 7. An additional beacon 1117 is attached to energy based dissection device 1130. Alternatively, a beacon may be an integral part of energy based dissection device 1130. Beacon 1117 transmits a signal having one or more characteristics (e.g., frequency, waveform, strength, content, etc.) that allow processor 1150 to identify the signal as that of the energy based dissection device.

One of skill in the art will appreciate the type of interpretative analysis needed in connection with any specific wave readout or other form of signal generated by nerve integrity monitoring devices and what immediate response is necessary to protect RLN (or other nerve, in the case of other types of surgeries to which this device is applicable) functionality.

One of skill in the art will also appreciate if full shutoff of energy to the energy based dissection device is required or if allowable to proceed at reduced on a minimal stimulus reading. Similarly, it may be desirable to have a manual override to continue with a procedure despite the risk disclosed. Surgeon expertise is not impacted, but rather enhanced by providing potential error correction and reaction time assistance.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

Each and every feature described herein, and each and every combination of two or more of such features, is included within the scope of the present invention provided that the features included in such a combination are not mutually exclusive.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A system for mapping a nerve, the system comprising:
an energy based dissection device;
a plurality of beacons adapted to be disposed in a tissue of a patient, each of said plurality of beacons adapted to:
  transmit one or more first electrical signals within the body; and
  receive one or more second energy signals; and
a processing device configured to:
  determine first locations associated with the plurality of beacons, a second location associated with the energy based dissection device, and a third location associated with a nerve within the tissue, based on the one or more second energy signals;

generate a mapping of the first locations, second location, and third location; and display the first locations, second location, and third location on a display device.

2. The system of claim 1, wherein the one or more second energy signals received by a first beacon among the plurality of beacons include electrical signals generated by a second beacon among the plurality of beacons.

3. The system of claim 2, wherein the one or more second energy signals further include second electrical signals emitted by the energy based dissection device.

4. The system of claim 1, wherein each of the plurality of beacons comprises a wired device.

5. The system of claim 1, wherein each of the plurality of beacons comprises a wireless device.

6. The system of claim 1, wherein the processing device comprises one of a personal computer, a laptop device, and a smart phone.

7. The system of claim 1, wherein each of the plurality of beacons comprises a transmitter.

8. The system of claim 7, wherein each of the plurality of beacons is adapted to be attached to the tissue.

9. The system of claim 1, wherein the energy based dissection device is configured to emit an energy burst for a predetermined time, at a predetermined frequency and at a predetermined power level, the energy burst being sufficient in frequency and power level to be detected by one or more of the plurality of beacons but insufficient in frequency and power level to damage tissue.

10. The system of claim 1, further comprising a manual override to the shutoff command.

11. A system for mapping a nerve, the system comprising:

a surgical device adapted to transmit an energy signal within a tissue of a patient;

a plurality of beacons adapted to be disposed in the tissue, each of the plurality of beacons comprising a transmitter and a receiver, each of the plurality of beacons being adapted to:

transmit one or more first electrical signals within the tissue at a respective frequency unique to the respective beacon; and receive one or more second energy signals; and a processing device configured to:

determine first locations associated with the plurality of beacons, a second location associated with the energy based dissection device, and a third location associated with a nerve within the tissue, based on the one or more second energy signals; and display a graphical representation of the first locations, second location, and third location on a display device.

12. The system of claim 11, wherein the one or more second energy signals received by a first beacon among the plurality of beacons include electrical signals generated by a second beacon among the plurality of beacons.

13. The system of claim 12, wherein the one or more second energy signals further include second electrical signals emitted by the surgical device.

14. The system of claim 12, wherein the one or more second energy signals further include second electrical signals reflected by the nerve.

15. The system of claim 11, wherein each of the plurality of beacons comprises a wired device.

16. The system of claim 11, wherein each of the plurality of beacons comprises a wireless device.

17. The system of claim 11, wherein the processing device comprises one of a personal computer, a laptop device, and a smart phone.

18. The system of claim 11, wherein one of the plurality of beacons is attached to the surgical device.

* * * * *